US006423220B1

(12) United States Patent
Fex

(10) Patent No.: US 6,423,220 B1
(45) Date of Patent: Jul. 23, 2002

(54) CHROMATOGRAPHIC METHOD AND CHROMATOGRAPHIC COLUMNS THEREFOR

(75) Inventor: Tomas Fex, Lund (SE)

(73) Assignee: Trikonex AB, Lund (SE)

( * ) Notice: Subject to any disclaimer, the term of this patent is extended or adjusted under 35 U.S.C. 154(b) by 73 days.

(21) Appl. No.: 09/709,387

(22) Filed: Nov. 13, 2000

Related U.S. Application Data

(63) Continuation of application No. PCT/SE99/00812, filed on May 12, 1999.

(30) Foreign Application Priority Data

May 14, 1998 (SE) ................................................ 9801687

(51) Int. Cl.⁷ ............................................. B01D 15/08
(52) U.S. Cl. .................. 210/198.2; 210/659; 210/198.2
(58) Field of Search ................................ 210/635, 656, 210/659, 198.2, 502.1; 422/70

(56) References Cited

U.S. PATENT DOCUMENTS

| | | | | |
|---|---|---|---|---|
| 4,235,716 A | * | 11/1980 | Halpaap | 210/198.2 |
| 4,322,342 A | | 3/1982 | Smithwick, Jr. et al. | 260/112.5 |
| 4,550,594 A | * | 11/1985 | Engstrom | 210/198.2 |
| 4,563,275 A | | 1/1986 | McEachern | 210/198.2 |
| 6,156,196 A | * | 12/2000 | Gao | 210/198.2 |

FOREIGN PATENT DOCUMENTS

DE           35 26 827           2/1986 .............. 210/198.2

OTHER PUBLICATIONS

Cover Page of WO99/58217 Nov. 18, 1999.
Form PCT/IB/308 PCT/SE99/00812 Nov. 26, 1999.
Form PCT/IPEA/402 PCT/SE99/00812 Nov. 2, 1999.
International Search Report for PCT/SE99/00812 Sept. 22, 1999.
PCT Request (Form PCT/RO/101) PCT/SE99/00812 May. 12, 1999.
Wiley–Interscience, A Division of John Wiley * Sons, Inc., vol. 3, 1970, Edmond S. Perry et al., "Progress in Separation and Purification", pp. 73–95.
PCT Preliminary Examination Report (Forms PCT/IPEA/409) PCT/SE99/00812 Aug. 9, 2000.

* cited by examiner

*Primary Examiner*—Ernest G. Therkorn
(74) *Attorney, Agent, or Firm*—Smith, Gambrell & Russell, LLP

(57) ABSTRACT

A chromatographic column for simultaneous purification of several compounds in a sample by dry column chromatography comprised by a plastic tube and containing a sorbent is described, wherein there is an empty volume on top of the sorbent large enough to hold the amount of developing solvent needed to develop the column, wherein the plastic material is transparent or semitransparent to UV and visible light and can be cut with a sharp object, and wherein the sorbent particle size is <40$\mu$ and contains a fluorescent material.

13 Claims, No Drawings

CHROMATOGRAPHIC METHOD AND CHROMATOGRAPHIC COLUMNS THEREFOR

This application is a continuation of International Application PCT/SE99/00812, filed May 12, 1999, and which is incorporated herein by reference.

FIELD OF THE INVENTION

The present invention relates to a dry chromatography method for the purification of from 1 mg to a few hundred mg quantities of compounds, to the type of columns and to the nature of the sorbents to be used for such separations. The method is suitable for purification of several compounds simultaneously, e.g. the purification of chemical libraries. As described in the present invention the method is well suited for automation since addition of the sample can be done in a simple and reproducible manner and since the eluent is simply added to the top of the column and in the exact amount needed for the separation.

BACKGROUND OF THE INVENTION

Combinatorial chemistry and high speed synthesis has become very important tools in medicinal chemistry. Large "libraries" of compounds are synthesised and subjected to High Throughput Screening (HTS) trying to identify novel structures with interesting biological activity. A "chemical library" may contain several thousands of compounds.

The chemical libraries may be prepared by conventional solution chemistry but solid phase methods are also being used. Many different types of automated synthesisers have been developed and automation is indeed a very important factor when trying to handle large numbers of compounds simultaneously. The compounds are commonly prepared in amounts of 1–100 mg, most often about 5–20 mg.

The quality of the library is highly dependent on the purity of the individual compounds present in the library. When a set of chemical reactions are applied to different substrates the yields of reaction may differ significantly, the end result being a chemical library where the purity of the compounds may vary considerably. Obviously, a simple method for the purification of several compounds at the same time would be very attractive. The method should preferably be suited for automation.

HPLC systems equipped with automated injectors can handle the separation of several samples. However the samples are separated sequentially on the same column and the column has to be regenerated after each run. Large amounts of solvents are needed and contamination of the column may often be a serious problem preventing long time use. Also, an extreme number of different fractions need to be collected and handled.

Dry column chromatography is a relatively old chromatographic method (Reviews: B. Loev and M. M. Goodman. in "Progress in Separation and Purification" 1970; vol. 3: 73–95. F. M. Rabel in M. Zeif and R. Speights (Eds.), "Ultrapuification", Dekker, New York 1972, p 157). The mixture to be purified is added to the top of a dry column of e.g. silica and the column is developed with a suitable solvent. When the solvent reaches the end of the column the separated compounds are located (e.g. by colour), the column cut into pieces and the desired compounds isolated by extraction. Typically column sizes of diam. 1–3 inches and length 10–20 inches have been used for purification of compound mixtures of several hundred mg to several grams. The particle size used has commonly been >63$\mu$.

Dry column chromatography has not been utilised for the simultaneous purification of large numbers of compounds, e.g. the purification of chemical libraries, and has never been subjected to automation in this connection.

Dry column chromatography has not been recognised as a suitable method for rapid purification of mg quantities of compounds on short columns.

As mentioned above dry column chromatography is an old chromatographic method and today it is practically never used. Obviously the advantages that are obtained when it is performed as described in the present invention have not been realised.

SUMMARY OF THE INVENTION

The object of the present invention is to eliminate the shortcomings and solve the problems stated above in connection with the known techniques for simultaneous purification of several compounds in a sample. This object is achieved by a chromatografic column of the type described by way of introduction having the features specified in the characterising part of claim 1. These and other features and advantages will appear from the following description and the subclaims. The present invention also relates to a method for simultaneous purification of several compounds in a chromatography column according to the present invention and also to use of such a column.

DESCRIPTION OF THE INVENTION

The present invention relates to a dry chromatography column to be used for rapid purification of from about 1 mg to a few hundred mg quantities of compounds. Several separations can be run simultaneously and the columns are very well suited for use in automated procedures.

According to the. present invention it has been found that short dry chromatography columns can be prepared by packing columns of suitable plastic materials with sorbents of small particle size, and that these columns can be used for rapid purification of small amounts of material. The top of the column contains an empty volume. Methods are provided whereby addition of the sample can be done in a simple and reproducible manner. The eluent is thereafter added to the top of the column and in the amount needed for the separation. The simplicity and the reproducibility of the chromatographic method described in the present invention make it well suited for automation. When the separations have been completed the desired compounds can be located on the columns, that particular part of the column cut out, and the compounds isolated by extraction.

Compared to conventional HPLC methods dry column chromatography utilises only small amounts of solvents and does not require handling of very large numbers of different fractions.

The columns of the present invention can be made of different plastic materials. These materials should be transparent or semitransparent to UV and visible light, to allow for location of the separated compounds on the column. The plastic should be compatible with the solvents to be used for the separations. Since the compounds are isolated by cutting out the desired part of the column it is important that the plastic is easy to cut with minimal deformation of the sorbent. Suitable thicknesses are between 0.5 to 3 mm, preferably 1 to 2 mm. Since the columns of the present invention are short they are still rigid enough to be easy to handle. Cutting can be done with a sharp object such as a knife, razorblade and the like. The columns are preferably cylindrical but other forms may be used.

Suitable plastic materials are those which can be used together with different organic solvents e.g. polyethylene, polypropylene and Teflon. Teflon has superior chemical resistance and is soft to cut. Polyethylene is softer than polypropylene. If very soft plastic materials are used, such columns may be put inside an outer shell. Combinations of plastic materials may also be used.

For the separations to proceed with acceptable speed the length of the column is generally less than 20 cm, preferably less than 15 cm. Columns of small diameter are easier to cut without deformation than wider columns. The diameter of the column may generally vary from about 0.3 to about 3 cm, preferably less than 1.5 cm. However, smaller columns may be used if almost analytical separations are desired and larger columns may be of use for separations of large amounts of material. For large amounts of material it may be more advantageous to use several columns in parallel. The problem that a compound moves slightly faster near the column wall is of greater significance for wider columns (c.f. B. Loev and M. M. Goodman. in "Progress in Separation and Purification" 1970; vol. 3: 73–95).

The column should have an empty volume above the sorbent preferably large enough to be able to hold the volume of solvent needed to develop the column. For a silica column this volume is generally 0.5 to 0.8 times the volume holding the sorbent. The volume may be indicated by a mark, a helpful feature when adding the developing solvent.

It is very important that the sample to be purified can be added to the column in a simple and reproducible manner, e.g. from a syringe or a pipette, so that it forms a narrow and uniform band at the top of the column. This is particularly difficult to accomplish for small columns. However, according to the present invention this problem has been solved by different methods as described below.

A portion of inert material without retaining capacity can be put on top of the sorbent. The sample, dissolved in a small amount of solvent is added and absorbs into the inert material. Subsequent addition of developing solvent transports the sample to the top of the sorbent where it forms a uniform band, whereafter development of the column proceeds in the normal manner. Inert materials, which can be used for the purpose above, are materials, which do not retain the sample and may e.g. be a plastic material such as polyamide. The inert material functions as a concentration zone. A thick filter made of similar materials may be used for the same purpose. The use of a small amount of relatively unpolar developing solvent in the beginning may be advantageous in order to minimise the band.

A different way to accomplish a uniform band at the top of the column involves the use of a plug, having one or several small holes, which covers the top of the column. The sample, dissolved in a small amount of solvent, is added to the column and is relatively slowly absorbed through the small holes onto the column in such a way that it forms a uniform band. The size of the holes, the number of holes and the exact shape of the plug may vary and is e.g. dependant on the diameter of the column, it being important that absorption onto the column proceeds in a uniform manner. The plug is preferably made of an inert plastic material and the thickness is typically 0.5–6 mm. The plug may be an integral part of the column.

Another opportunity is to, on top of the column, use a porous filter, which has the capability to absorb and distribute the sample solution within itself, before the solution enters onto the top of the sorbent. Such filters may e.g. be made of different plastic materials. Filters of polyethylene may be very useful.

Still another opportunity is to absorb the sample into a porous plug, which can subsequently be put on top of the column. The plug should cover the surface of the column and should be made from a material, which does not retain the compounds when the eluting solvent is added, the compounds being transferred directly onto the top of the column.

A preferred way to accomplish a uniform addition of the sample is to first "wet" the column with a small amount of solvent. Subsequent addition of the sample solution allows It to be absorbed onto the column more slowly and this in turn results in a uniform band. This type of sample addition has not been described previously in combination with dry column chromatography.

Various combinations of the methods described above and which give a uniform band on top of the column may also be used.

It is important that the column can be cut into pieces in a reproducible manner and that the sorbent is retained in the piece that is cut out. According to the present invention it has been found that this is best accomplished when the sorbent is of small particle size and that particles of irregular form may stick together better than spherical particles. The problem is especially relevant when volatile solvents are being used to develop the column, since when the solvents evaporate the piece of column which is cut out dries. For columns with large diameters the problem may be of greater importance than for columns with small diameters.

As is evident from that stated above, the particle size of a sorbent in the column according to the present invention is of great importance, and several factors have to be considered and balanced with a view to obtaining good separation characteristics of the column. It is well known that sorbents having small particle sizes are difficult to dry pack, as aggregates are formed leaving too long an eluation time. In contrast, sorbents having large particle sizes are easier to dry pack, resulting in columns with a shorter eluation time. However, in the latter case the separation characteristics are impaired, and when the column is cut into pieces, the sorbent is likely to fall out of the column.

The inventor has surprisingly found that columns having dimensions here defined can be dry packed in a satisfactory way with sorbents having a small particle size. In particular, Grace silica with a particle size of 6–35 $\mu$m has appeared to give very favourable flow characteristics, probably due to a small amount of very small particles.

When silica is used as sorbent it is preferred that the particle size is <63$\mu$ and <40$\mu$ is even more preferable. Silica's with particle sizes ranging between 5–40$\mu$ or 6–35$\mu$ are suitable. It is important to choose a silica which allows the columns to be developed as rapidly as possible. This also means that longer columns can be produced. According to the present invention it has surprisingly been found that a silica of particle size 6–35$\mu$ from Grace is much superior to a Matrex silica of particle size 6–35$\mu$ from Amicon which in turn is superior to a silica of particle size 5–40$\mu$ from Merck. When examined in the microscope the Grace silica seem to contain a minimum of very fine particles and this might explain its superior properties when used for dry column chromatography purposes. A column packed with silica from Grace is developed about 50% faster than a column with Matrex silica from Amicon. Yet another advantage with the Grace silica is that it is easier to pack than the other ones. Still another advantage of this silica is that it is available at a low price, which is important since the columns are only utilised once.

When aluminium oxide is used as sorbent, similar particle sizes <63µ and <40µ are also suitable.

Sorbents having small particle size generally give sharper separations. For this reason a silica with particle size <25µ e.g. 15–25µ, or even better 5–20µ, may be suitable.

Sorbents having small particle size and having spherical particles give good separations.

Silica and aluminium oxide are preferred sorbents, but in principle all sorbents used for chromatography can be utilised in the present invention. The silica or aluminium oxide is preferably deactivated (c.f. B. Loev and M. M. Goodman. in "Progress in Separation and Purification" 1970; vol. 3: 73–95). When the sorbent is deactivated in the open air the amount of water which is absorbed may vary depending on e.g. humidity.

The sorbents may have been pre-treated in various ways to make them suitable for different type of separations. E.g. they may have been conditioned in the presence of suitable chemicals. Silica to be used for the separation of amines may thus be conditioned in vapour containing ammonia or other volatile amines. Another way to condition the column is to put the ready column in such vapours. In this case the conditioning process may be accelerated by drawing, e.g. using vacuum, amine vapours through the column.

It is preferred that the sorbents (c.f. above) and the different parts of the columns (e.g. filters) are available at relatively low prices since they are only utilised once.

Various binders can be used in order to "glue" the sorbent together and thus improve the properties of the column regarding performance when being cut. Calcium sulphate is a binder often used in connection with TLC, and is useful for the purpose above. The use of a binder and the amount of binder to be used may vary according to the specific application, but generally binders may be of greater importance for columns of wider diameter.

It is important that when a mixture has been separated on the column that the individual components can be visualised. This may be accomplished by well known techniques used e.g. in TLC. Commonly a fluorescent material is incorporated into the sorbent, giving dark bands where UV absorbing components are located. Some compounds may be fluorescent by themselves when irradiated with light of appropriate wavelength, and of course coloured compounds are easily seen. For compounds, which do not absorb UV-light, the position of the compound may be estimated by comparison with TLC $R_f$-values. Another opportunity when the compounds cannot be visualised is to cut the column in pieces and analyse each piece individually.

The columns may be packed by known dry packing techniques. Uniform and dense packing is important for satisfactory chromatographic performance. The columns can e.g. be packed by simultaneous addition of sorbent and tapping the bottom of the column firmly against the surface. Tapping is continued until the sorbent is densely packed. According to the present invention it has been found that a Grace silica of particle size 6–35µ is very easy to dry pack. Vacuum may be applied during packing. Pressure may also be used. The sorbent is confined on the column by filters on the top and at the bottom.

It is generally believed in the art that sorbents containing particles <20µ cannot be dry packed. However according to the present invention it has been found that this type of packing works well for dry chromatography, especially for the Grace silica described above.

The columns may have a scale on the outside. This makes it possible to determine $R_f$-values, which may be used as part of compound identity, and may be of help when examining the column in order to decide which pieces to cut out.

The solvents used to develop the column may be all those known in the art. It has been stated (B. Loev and M. M. Goodman. in "Progress in Separation and Purification" 1970; vol. 3: 73–95) that the use of solvent mixtures may be disadvantageous. According to the present invention it has been found that solvent mixtures work well.

It is of some importance to analyse the column and to cut out the desired fractions directly after it has been developed. Otherwise the compounds will diffuse and this will result in band broadening.

In a modification of the present invention the sample to be separated is allowed to be absorbed into the filter and sorbent at the bottom of the column. Development of the column is subsequently achieved by putting the column in the desired development solvent and allowing this to ascend through the column by capillary action. For these columns it is of course not necessary that they have an empty volume on top of the column.

It is important to be able to cut the columns into small pieces with a minimum of deformation. Cutting devices that are able to provide support around the column are suitable for this purpose and these are also within the scope of the present invention. A preferred cutting device is characterised in that it supports the column on both sides of the cutting zone.

The type of chromatography described in the present invention is highly suited for automation. Various robots and machines can be used to add samples and developing solvents to large numbers of columns. The use of automation together with the present type of chromatography is also within the scope of the present invention.

The handling of several columns simultaneously is of great interest in connection with purification of chemical libraries and this particular utilisation lies within the scope of the present invention. For combinatorial libraries it may not be necessary to obtain extremely pure compounds but purities of 80–90% may be sufficient. The present invention is very useful for this purpose.

EXAMPLES

Example 1

A tube of Teflon (i.d.=4 mm) was packed with TLC grade silica (Merck, silica gel 60 $PF_{254}$ containing gysum, particle size 5–40 µm), which had been kept in the open air at room temp. over night in order to deactivate the gel. The column was tapped against the table surface during the packing procedure in order to accomplish dense packing. At the top was added a small amount of polyamide and the column was stoppered with a plug of cotton. The height of the column was 79 mm of silica and 5 mm of polyamide. 5 mg of a 1:1 mixture of 11-hydoxy-progesterone and 17-hydroxy-progesterone in 0.1 ml of methylene chloride/ethanol (8:2) was added. The column was developed by adding 2-butanon/heptane (1:1). When the solvent front had reached the bottom of the column it was examined in a UV-box. The piece 53–61 mm and the piece 35–45 mm from the beginning of the silica gel part of the column were cut out. The first piece contained pure 17-hydroxy-progesterone and the second piece contained 11hydroxyprogesterone (slightly contaminated with the 17-hydroxy isomer) which could be isolated by extraction.

Example 2

A column similar to the one in example 1 was prepared. The height of silica was 76 mm and the height of polyamide was 5 mm. 10 mg of a 1:1 mixture of 4-Br-methyl benzoate and 3-hydroxy-methyl benzoate in 0.1 ml of ethyl acetate/heptane (4:6) was added and the column developed using the same solvent mixture. When the solvent front had reached the bottom of the column it was examined in a UV-box. The piece 55–64 mm and the piece 41–51 mm from the beginning of the silica gel part of the column were cut out. The first one contained pure 4-Br-methyl benzoate and the second pure 3-hydroxy-methyl benzoate.

Example 3

A tube of polypropene (i.d.=9 mm) was stoppered at the bottom with a polyethylene filter and a column was packed with silica as described in example 1. At the top was added a small amount of polyamide and the column was stoppered with a polyethylene filter. The height of the column was 36 mm of silica and 4 mm of polyamide. 20 mg of a 1:1 mixture of 4-Br-methyl benzoate and 3-hydroxy-methyl benzoate in 0.2 ml of ethyl acetate/heptane (4:6) was added and the column developed using the same solvent mixture. When the solvent front had reached the bottom of the column it was examined in a UV-box. The piece 23–31 mm and the piece 13–20 mm from the beginning of the silica gel part of the column were cut out. The first one contained pure 4-Br-methyl benzoate and the second pure 3-hydroxy-methyl benzoate.

In a similar experiment a tube of polyethylene (i.d.=12 mm) packed with 3.2 g (height of column=55 mm) of sorbent was used to achieve separation of 50 mg of the same mixture.

Example 4

A tube of polypropylene (i.d.=5 mm) was stoppered at the bottom with a polyethylene filter and a column was packed with silica as described in example 1. On the top of the silica was put another polyethylene filter and on top of this a Teflon plug (thickness=3 mm) having five small holes (d=0.5 mm). The height of silica was 32 mm. 5 mg of a 1:1 mixture of 4-Br-methyl benzoate and 3-hydroxy-methyl benzoate in 0.05 ml of ethyl acetate/heptane (4:6) was added and the column developed using the same solvent mixture. When the solvent front had reached the bottom of the column it was examined in a UV-box. The piece 22–28 and the piece 13–20 mm from the beginning of the silica gel part of the column were cut out. The first one contained pure 4-Br-methyl benzoate and the second pure 3-hydroxy-methyl benzoate.

Example 5

A tube of polyethylene (i.d.=9 mm) was stoppered with a polyethylene filter (20$\mu$) and the column was packed with 2 g of deactivated silica (6–35$\mu$) to which about 1% of fluorescent material had been added. On the top was put another filter. The height of the column was 68 mm. 20 mg of a 1:1 mixture of 4-Br-methyl benzoate and 3-hydroxy-methyl benzoate in 0.1 ml of ethyl acetate/heptane (4:6) was added whereafter two portions of about 0.1 ml of solvent mixture were allowed to absorb onto the column. The column was then developed using the same solvent mixture. When the solvent front had reached the bottom of the column it was examined in a UV-box. The piece 44–55 and the piece 28–42 mm from the beginning of the silica gel part of the column were cut out. The first one contained pure 4-Br-methyl benzoate and the second pure 3-hydroxy-methyl benzoate.

Example 6

A tube of polyethylene (i.d.=9 mm) was stoppered with a polyethylene filter (20$\mu$) and the column was packed with 2 g of deactivated silica (6–35$\mu$) to which about 1% of fluorescent material had been added. On the top was put another filter and on top of this a Teflon plug (3 mm thick and having 13 holes with a diam. of 0.5 mm). The height of the column was 67 mm. 20 mg of a 1:1 mixture of 4-Br-methyl benzoate and 3-hydroxy-methyl benzoate in 0.1 ml of ethyl acetate/heptane (4:6) was added and the column developed using the same solvent mixture. When the solvent front had reached the bottom of the column it was examined in a UV-box. The piece 39–49 mm and the piece 24–35 mm from the beginning of the silica gel part of the column were cut out. The first contained pure 4-Br-methyl benzoate and the second pure 3-hydroxy-methyl benzoate.

In a similar experiment a column was prepared with 2 g of Merck Lichroprep Si 60 (15–25 $\mu$m) to which about 1% of fluorescent material had been added and which had been deactivated. The height of the column was 54 mm. The piece at 36–45 mm contained 4-Br-methyl benzoate and the piece at 22–33 mm contained 3-hydroxy-methyl benzoate.

In a similar experiment a column was prepared with 2 g of Merck Lichroprep Si (5–20 $\mu$m) to which about 1% of fluorescent material had been added and which had been deactivated. The height of the column was 60 mm. The piece at 45–53 mm contained 4-Br-methyl benzoate and the piece at 28–38 mm contained 3-hydroxy-methyl benzoate.

Example 7

A tube of polypropylene (i.d.=5 mm) was stoppered at the bottom with a polyethylene filter and the column was packed with silica as described in example 4. The height of silica was 29 mm. 4 mg of a 1:1 mixture of 2,4-dimethylbenzoic acid and 2,6-dimethoxybenzoic acid in 0.05 ml of ethyl acetate/ethanol (9:1) was added and the column developed using ethyl acetate/heptane/acetic acid (1:3:0.2). When the solvent front had reached the bottom of the column it was examined in a UV-box. The piece 14–23 mm and the piece 5–12 mm from the beginning of the silica gel part of the column were cut out. The first one contained pure 2,4-dimethylbenzoic acid and the second pure 2,6-dimethoxybenzoic acid.

Example 8

A column similar to the one in example 4 was prepared utilising Merck Lichroprep Si 60 (15–25 $\mu$m) to which about 1% of fluorescent material had been added and which had been deactivated. The height of the silica was 36 mm. 5 mg of a 1:1 mixture of 4-Br-methyl benzoate and 3-hydroxy-methyl benzoate in 0.05 ml of ethyl acetate/heptane (4:6) was added and the column developed using the same solvent mixture. When the solvent front had reached the bottom of the column it was examined in a UV-box. The piece 28–33 mm and the piece 14–20 mm from the beginning of the silica gel part of the column were cut out. The first one contained pure 4-Br-methyl benzoate and the second pure 3-hydroxy-methyl benzoate.

Example 9

A column similar to the one in example 4 was prepared utilising Merck Lichroprep Si 100 (25–40 $\mu$m) to which about 1% of fluorescent material had been added and which had been deactivated. The height of the silica was 36 mm. 5 mg of a 1:1 mixture of 4-Br-methyl benzoate and 3-hydroxy-methyl benzoate in 0.05 ml of ethyl acetate/heptane (4:6) was added and the column developed using the same solvent mixture. When the solvent front had reached the bottom of the column it was examined in a UV-box. The piece 25–32 mm and the piece 16–24 mm from the beginning of the silica gel part of the column were cut out. The first one contained pure 4-Br-methyl benzoate and the second pure 3-hydroxy-methyl benzoate.

Example 10

TLC grade silica (Merck, silica gel 60 $PF_{254}$ containing gypsum, particle size 5–40 μm) was kept for some days in a closed container containing an open test tube with conc. ammonia. This silica was utilised to prepare a column similar to the one in example 4. The height of the silica was 27 mm. 5 mg of a 1:1 mixture of 1-naphtylamine and 3,4-dimethoxyphenethylamine in 0.05 ml of ethyl acetate/ethanol (1:1) was added and the column developed using the same solvent mixture. When the solvent front had reached the bottom of the column it was examined in a UV-box. The piece 9–15 mm and the piece 3–8 mm from the beginning of the silica gel part of the column were cut out. The first one contained pure 1-naphtylamine and the second pure 3,4-dimethoxyphenethylamine.

Example 11

A tube of Teflon (i.d.=4 mm) was packed with TLC grade aluminium oxide (Merck, aluminium oxide 150 $F_{254}$ neutral, type T, particle size 5–40 μm), which had been kept in the open air at room temp. over night in order to deactivate the gel. The column was tapped against the table surface during the packing procedure in order to accomplish a dense packing. At the top was added a small amount of polyamide and the column was stoppered with a plug of cotton. The height of the column was 57 mm of silica and 5 mm of polyamide. 5 mg of a 1:1 mixture of 4-Br-methyl benzoate and 3-hydroxy-methyl benzoate in 0.05 ml of ethyl acetate/heptane (1:9) was added and the column developed using the same solvent mixture. When the solvent front had reached the bottom of the column it was examined in a UV-box. The piece 39–54 mm and the piece 0–12 mm from the beginning of the aluminium oxide gel part of the column were cut out. The first one contained pure 4-Br-methyl benzoate and the second pure 3-hydroxy-methyl benzoate.

Example 12

A tube of Teflon (i.d.=4 mm) was packed with TLC grade aluminium oxide (Merck, aluminium oxide 150 $F_{254}$ neutral, type T, particle size 5–40 μm), which had been kept in the open air at room temp. over night in order to deactivate the gel. The column was tapped against the table surface during the packing procedure in order to accomplish a dense packing. At the top was added a small amount of polyamide and the column was stoppered with a plug of cotton. The height of the column was 52 mm of silica and 5 mm of polyamide. 5 mg of a 1:1 mixture of 4-Br-methyl benzoate and 1,2,3-timethoxybensene in 0.05 ml of ethyl acetate/heptane (1:9) was added and the column developed using the same solvent mixture. When the solvent front had reached the bottom of the column it was examined in a UV-box. The piece 38–45 mm and the piece 29–37 mm from the beginning of the aluminium oxide gel part of the column were cut out. The first one contained pure 4-Br-methyl benzoate and the second pure 1,2,3-timethoxybensene.

Example 13

A tube of Teflon (i.d.=4 mm) was packed with Merck Lichroprep Si 60 (15–25 μm). The height of the column was 90 mm and it contained 0.87 g of sorbent. The column was developed with ethyl acetate/heptane (2:3) and the time of development was measured. The solvent front had reached 41 mm after 5 min, 59 mm after 10 min and 86 mm after 20 min.

A similar column was packed TLC grade silica (Merck, silica gel 60 $PF_{254}$ containing gypsum, particle size 5–40 μm). The height of the column was 90 mm and it contained 0.85 g of sorbent. The column was developed with ethyl acetate/heptane (2:3) and the time of development was measured. The solvent front had reached 21 mm after 5 min, 33 mm after 10 min, 50 mm after 20 min and 65 mm after 30 min.

Example 14

Three different types of silica were used to pack columns, each containing 2.0 g of packing material.
A. Merck TLC silica 5–40μ. Height 69 mm.
B. Amicon Matrex silica 6–35μ. Height 70 mm.
C. Grace silica 6–35μ. Height 66 mm.
To each column was added 3.0 ml of ethyl acetate. After 5 min the distance that had been reached by the solvent front was measured. A 23 mm. B 32 mm. C 49 mm.

Example 15

A tube of Teflon (i.d.=4 mm) was packed with TLC grade silica (Merck, silica gel 60 $PF_{254}$ containing gypsum, particle size 5–40 μm). The height of the column was 55 mm and there were pieces of cotton (4 mm) on both sides. 3 mg of a 1:1 mixture of 4-amino-3-nitrotoluene and N-methyl-2-nitroaniline in 50 μl of methylene chloride was absorbed into the bottom of the column and this was developed in ascending mode using methylene chloride/heptane (5:2). The piece of the column 33–40 mm and the piece 26–32 mm from the bottom (of the silica) were cut out containing 4-amino-3-nitrotoluene and N-methyl-2-nitroaniline respectively.

Example 16

A 20μ polyethylene filter (d=9 mm, 1.6 mm thick) was put on top of a filter paper, Approximately 20–30 μl of solvent (ethyl acetate) was absorbed in the filter before it entered into the filter paper. For a similar filter (d=12 mm, 2.0 mm thick) the volume was about 50–60 μl.

Example 17

A polyethylene tube (i.d.=9 mm. o.d.=12 mm. l=12.5 mm) was packed with Grace silica 6–35μ containing about 2% of fluorescent material. The height of the column was 66 mm. 0.3 ml of methylene chloride was added to "wet" the column. 5 mg of a 1:1 mixture of 4-methoxy-2-nitroaniline and N-methyl-2-nitroaniline in 0.2 ml of methylene chloride was added. Two portions of methylene chloride were added and allowed to absorb into the column and subsequently 2.5 ml of methylene chloride was added and the column was allowed to develop. The piece of the column 18–27 mm and the piece 35–47 mm from the top were cut out containing 4-methoxy-2-nitroaniline and N-methyl-2-nitro-aniline respectively.

What is claimed is:
1. A chromatographic column for simultaneous purification of several compounds in a sample by dry column chromatography comprised by a plastic tube and containing a sorbent, characterised in that there is an empty volume on top of the sorbent large enough to hold the amount of developing solvent needed to develop the column, in that the plastic material is transparent or semitransparent to UV and visible light and can be cut with a sharp object, and in that the sorbent particle size is <40μ and contains a fluorescent material.

2. A chromatographic column according to claim 1 characterised in that it is packed with a Grace silica 6–35μ, or a silica with similar flow characteristics.

3. A chromatographic column according to claim 1 characterised in that the height of the column is <15 cm and/or that the inner diameter of the column is <1.5 cm and in that the empty volume is at least 0.5 times the volume of the column containing the sorbent.

4. A chromatographic column according to claim 1 characterised in that it is adapted to be used for separations of <0.2 g of material.

5. A chromatographic column according to claim 1 characterised in that on top of the sorbent there is a concentration zone of an inert material, or in that on top of the sorbent there is a filter which has the capability to absorb and distribute the sample solution within the filter before it enters onto the top of the sorbent, or in that the top of the column is covered by a plug having one or several small holes.

6. A chromatographic column according to claim 1 characterised in that the sorbent has been preconditioned in a suitable atmosphere.

7. A chromatographic column according to claim 1 characterised in that it is adapted to be used for ascending chromatography.

8. Chromatographic columns according to claim 1 characterised in that they are adapted to be used in a procedure, where several columns are developed simultaneously.

9. Chromatographic columns according to claim 8, wherein the columns are adapted to be used in an automated procedure.

10. Chromatographic columns according to claim 9, wherein the columns are adapted to be used in a purification of a chemical library.

11. Chromatographic columns according to claim 8, wherein the columns are adapted to be used in a purification of a chemical library.

12. A method for simultaneous purification of several compounds in a sample, in a dry chromatography column according to claim 1, wherein the column is first "wetted" by adding a small amount of eluent, the sample is then added, followed by adding the remaining part of eluent to be used, the sorbent containing part of the column is cut when the eluent has reached the end of the column and the compounds have been located in said part, and the compounds are isolated by extraction.

13. A method according to claim 12, wherein the sample is a chemical library.

* * * * *